(12) United States Patent  
Walach

(10) Patent No.: US 11,850,002 B2  
(45) Date of Patent: Dec. 26, 2023

(54) THREE-DIMENSIONAL MODEL FOR SURGICAL PLANNING

(71) Applicant: International Business Machines Corporation, Armonk, NY (US)

(72) Inventor: Eugeniusz Walach, Haifa (IL)

(73) Assignee: International Business Machines Corporation, Armonk, NY (US)

( * ) Notice: Subject to any disclaimer, the term of this patent is extended or adjusted under 35 U.S.C. 154(b) by 1555 days.

(21) Appl. No.: 16/036,232

(22) Filed: Jul. 16, 2018

(65) Prior Publication Data

US 2020/0015893 A1 Jan. 16, 2020

(51) Int. Cl.
*A61B 8/00* (2006.01)
*A61B 34/10* (2016.01)
*B29C 64/386* (2017.01)
*B33Y 80/00* (2015.01)
*G16H 10/60* (2018.01)
(Continued)

(52) U.S. Cl.
CPC ............ *A61B 34/10* (2016.02); *B29C 64/386* (2017.08); *A61B 5/0035* (2013.01); *A61B 8/5261* (2013.01); *A61B 2034/102* (2016.02); *A61B 2034/105* (2016.02); *A61B 2034/107* (2016.02); *A61B 2034/108* (2016.02); *A61B 2034/256* (2016.02); *A61B 2090/363* (2016.02); *A61B 2090/3983* (2016.02); *B22F 10/28* (2021.01); *B22F 12/53* (2021.01); *B29L 2031/7532* (2013.01); *B33Y 10/00* (2014.12); *B33Y 50/02* (2014.12); *B33Y 70/10* (2020.01); *B33Y 80/00* (2014.12); *G16H 10/60* (2018.01); *G16H 30/40* (2018.01); *G16H 50/50* (2018.01)

(58) Field of Classification Search
CPC .............. A61B 34/10; A61B 2034/102; A61B 2034/105; A61B 2034/107; A61B 2034/108; A61B 2090/363; A61B 2090/3983
See application file for complete search history.

(56) References Cited

U.S. PATENT DOCUMENTS

2008/0081982 A1* 4/2008 Simon ..................... A61B 34/25  
600/407
2008/0123910 A1* 5/2008 Zhu ......................... A61B 34/20  
382/128

(Continued)

FOREIGN PATENT DOCUMENTS

WO 2016154571 A1 9/2016

OTHER PUBLICATIONS

Cahoon, S., "Surgical Models and 3D Printing in the Medical Profession", Discover how 3D printing is transforming and revolutionizing the healthcare industry, MatterHackers, Feb. 6, 2018, 12 pages.

(Continued)

*Primary Examiner* — Joel F Brutus  
(74) *Attorney, Agent, or Firm* — Stosch Sabo

(57) ABSTRACT

Pre-surgical planning can use a three-dimensional model of an anatomical structure having a plurality of fiduciary points and a surgical mark integrated into the three-dimensional model using a contrast material. A model image of the three-dimensional model can be superimposed with a diagnostic image of the anatomical structure using the plurality of fiduciary points in order to create a superimposed image.

20 Claims, 8 Drawing Sheets

(51) Int. Cl.
  *A61B 90/00* (2016.01)
  *B33Y 50/02* (2015.01)
  *B29L 31/00* (2006.01)
  *A61B 5/00* (2006.01)
  *B33Y 10/00* (2015.01)
  *A61B 8/08* (2006.01)
  *G16H 50/50* (2018.01)
  *A61B 34/00* (2016.01)
  *B33Y 70/10* (2020.01)
  *G16H 30/40* (2018.01)
  *B22F 10/28* (2021.01)
  *B22F 12/53* (2021.01)

(56) References Cited

U.S. PATENT DOCUMENTS

| | | | | |
|---|---|---|---|---|
| 2010/0286568 | A1* | 11/2010 | Xia | A61B 5/1127 600/587 |
| 2013/0172731 | A1* | 7/2013 | Gole | A61B 6/506 600/424 |
| 2014/0303990 | A1 | 10/2014 | Schoenefeld et al. | |
| 2015/0025666 | A1 | 1/2015 | Olivieri et al. | |
| 2016/0129637 | A1 | 5/2016 | Zhou et al. | |
| 2016/0271379 | A1* | 9/2016 | Pouliot | A61B 6/037 |
| 2016/0324664 | A1* | 11/2016 | Piron | A61F 2/4601 |
| 2017/0217102 | A1 | 8/2017 | Mansi et al. | |

OTHER PUBLICATIONS

Newmarker, C., "3D printed organ models are getting way better: here's how", Medical Design & Outsourcing: A Mass Device Resource, Dec. 6, 2017, 3 pages https://www.medicaldesignandoutsourcing.com/3d-printed-organ-models-getting-better/.

Unknown, "New Advancements in 3D Printing Medical Models", stratasys direct manufacturing, 7 pages https://www.stratasysdirect.com/industries/medical/better-breakthrough-anatomical-models.

* cited by examiner

THREE-DIMENSIONAL MODEL FOR SURGICAL PLANNING

BACKGROUND

The present disclosure relates to surgical planning, and, more specifically, to using three-dimensional (3D) models in surgical planning.

3D printing is a form of rapid prototyping/additive manufacturing useful for rapidly manufacturing low quantities of customized models. Customized models can be generated using computer-aided design (CAD), a 3D scanner, and/or photogrammetry software. Customized models can be fabricated using a 3D printer.

SUMMARY

Aspects of the present disclosure are directed toward a computer-implemented method comprising selecting a plurality of fiduciary points on a diagnostic image of an organ and generating a file storing instructions for printing a three-dimensional model of the organ based on the diagnostic image. The file can store instructions for a base material and a first contrast material. The file can store instructions for printing the plurality of fiduciary points and a surgical mark using the first contrast material. The method can further comprise receiving a model image of the three-dimensional model, where the first contrast material is visible in the model image, and outputting a superimposed image file by superimposing the diagnostic image with the model image using the plurality of fiduciary points.

Aspects of the present disclosure are directed toward a system comprising a user interface, a processor, and a computer-readable storage medium storing program instructions, which, when executed by the processor a configured to cause the processor to perform a method comprising aligning a first plurality of fiduciary points of a diagnostic image with a second plurality of fiduciary points of a model image to create a superimposed image. The diagnostic image can illustrate an anatomical structure, and the model image can illustrate a surgical mark. The method can further comprise saving the superimposed image in the computer-readable storage medium and displaying the superimposed image on the user interface. The model image can comprise an image of a three-dimensional model replicating the anatomical structure. The second plurality of fiduciary points and the surgical mark can comprise a contrast material integrated in the three-dimensional model.

Aspects of the present disclosure are directed toward an apparatus comprising a three-dimensional model. The three-dimensional model can comprise a thermoplastic base material geometrically approximating an organ. The three-dimensional model can further comprise a plurality of fiduciary points integrated in the three-dimensional model, where the plurality of fiduciary points comprises a first contrast material. The three-dimensional model can further comprise a first surgical mark integrated in the three-dimensional model, where the first surgical mark comprises a second contrast material.

The above Summary is not intended to illustrate each embodiment of, or every aspect of, the present disclosure.

BRIEF DESCRIPTION OF THE DRAWINGS

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure.

Figure 1:
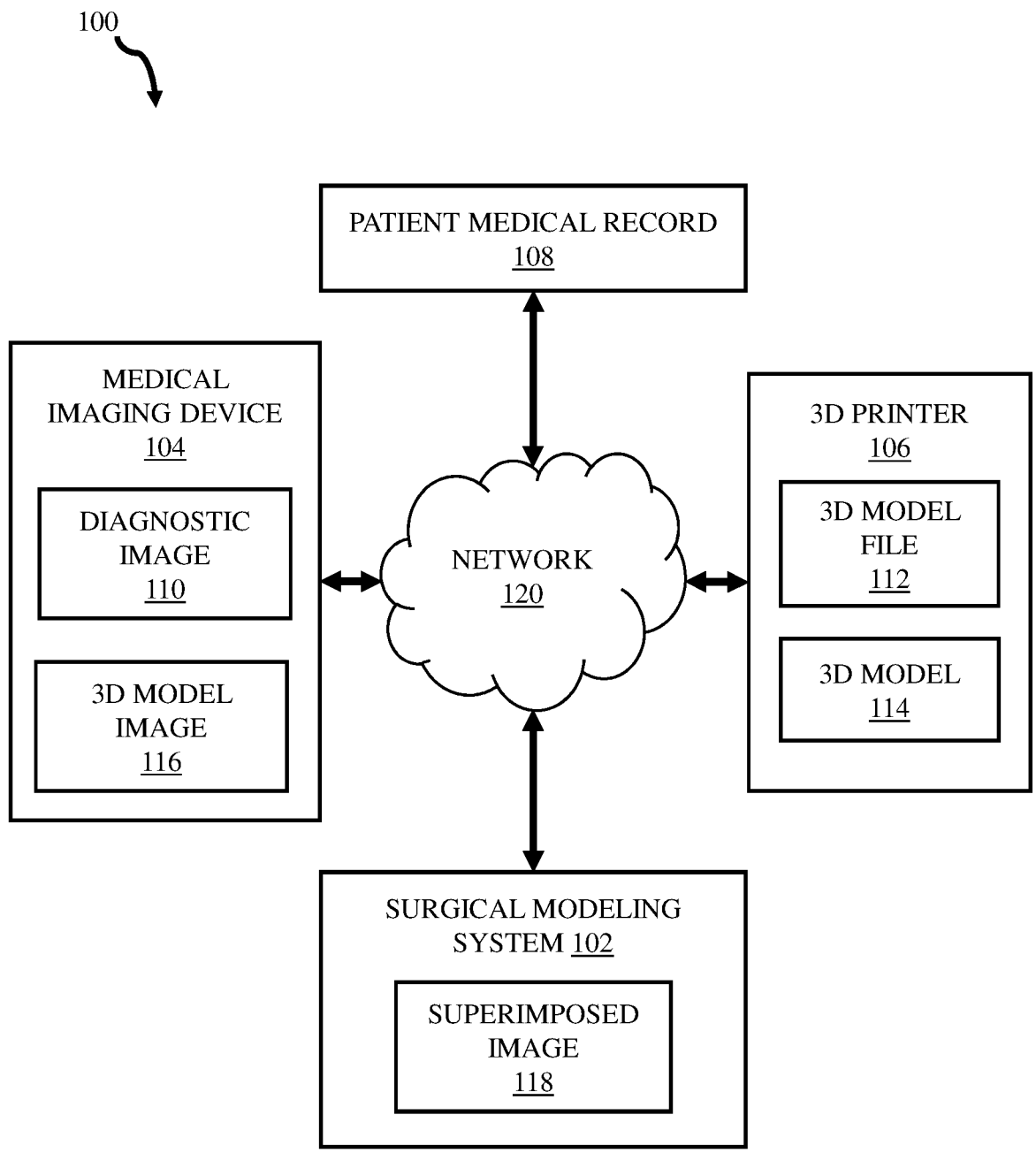
FIG. 1 illustrates a block diagram of an example medical system, in accordance with some embodiments of the present disclosure.

While the present disclosure is amenable to various modifications and alternative forms, specifics thereof have been shown by way of example in the drawings and will be described in detail. It should be understood, however, that the intention is not to limit the present disclosure to the particular embodiments described. On the contrary, the intention is to cover all modifications, equivalents, and alternatives falling within the spirit and scope of the present disclosure.

DETAILED DESCRIPTION

Aspects of the present disclosure are directed toward surgical planning, and, more specifically, to using 3D models in surgical planning. While the present disclosure is not necessarily limited to such applications, various aspects of the present disclosure can be appreciated through a discussion of various examples using this context.

Surgical planning can involve planning incisions, cuts, lacerations, extractions, implants, sutures, and/or other aspects of a surgical procedure. Pre-surgical planning can be useful to improve speed, accuracy, and safety of surgeries.

One challenge associated with pre-surgical planning involves the variable features, shapes, sizes, and locations of anatomical structures in individual patients. These differences, based on age, weight, height, body shape, body composition, gender, medical history, and other factors, make each surgical procedure unique. These unique surgical procedures require advanced planning to execute correctly. However, there are limited resources available for modeling the unique aspects of each surgical procedure.

Aspects of the present disclosure overcome the challenge of modeling surgical procedures by fabricating a 3D model of an anatomical structure based on one or more diagnostic images of the anatomical structure (e.g., computed tomography (CT) images), integrating surgical marks into the 3D model using contrast materials (e.g., during fabrication based on a physician's input, or post-fabrication based on a physician manually marking, or otherwise manipulating, the model), generating a model image of the 3D model (e.g., a CT image), and superimposing the model image with the diagnostic image to create a superimposed image.

In some embodiments, the model image can be superimposed with the diagnostic image using respective fiduciary points (e.g., fiducials, fiducial markers, etc.) on each image. In some embodiments, the 3D model can be fabricated by a 3D printer with a base material (e.g., a material that is invisible in a medical scan) and one or more contrast materials (e.g., materials that are visible in a medical scan) that are used to indicate fiduciary points and/or surgical marks.

In some embodiments, a surface of the 3D model is marked using an ink that is visible in a medical scan of the 3D model. Thus, aspects of the present disclosure enable a physician to perform pre-surgical planning by manually marking the 3D model in order to view the manual markings on the superimposed image. In some embodiments, a physician can mark the surface of the 3D model. In some embodiments, a physician can also mark an interior of the model. For example, a physician can perform a mock surgery on the 3D model to implant a medical device at a desired location. The physician can subsequently use the superimposed image to review the mock surgical procedure and/or plan the real surgical procedure.

Aspects of the present disclosure provide numerous advantages. First, aspects of the present disclosure integrate surgical marks into a 3D model of an organ, thereby allowing a healthcare practitioner to view the surgical marks in three-dimensions.

Second, aspects of the present disclosure enable a physician to mark the 3D model using an ink that is visible in a medical image (e.g., CT image) of the 3D model, thereby allowing the physician to perform pre-surgical planning on the 3D model. In some embodiments, a surface of the 3D model is marked and/or an internal portion of the 3D model is marked (e.g., as a result of a physician making a cut and inserting the contrast material inside of the cut).

Third, aspects of the present disclosure create a superimposed image illustrating the surgical marks on the 3D model on a superimposed image (e.g., a diagnostic image of the organ superimposed on a model image of the 3D model), thereby allowing a physician to view the surgical marks on a medical image of the organ (e.g., a CT image). As is understood by the one skilled in the art, viewing a pre-surgical plan on both a 3D model and a two-dimensional superimposed image is beneficial to a physician for planning, understanding, and/or communicating various aspects of a surgical procedure.

Fourth, aspects of the present disclosure enable a physician to review the accuracy of the surgical procedure (e.g., by identifying differences between the surgical marks in the diagnostic image with the corresponding post-operative surgical marks in a post-operative diagnostic image).

The aforementioned advantages are example advantages and not all advantages are listed. Furthermore, embodiments of the present disclosure exist that can contain all, some, or none of the aforementioned advantages while remaining within the spirit and scope of the present disclosure.

For simplicity, aspects of the present disclosure are discussed with respect to diagnostic images and 3D models of an "organ", however, this should not be construed to be limiting. To the contrary, aspects of the present disclosure are applicable to anatomical features other than organs such as, but not limited to, bones, tendons, ligaments, muscles, and other anatomical features. Furthermore, aspects of the present disclosure are applicable to combinations of any of the aforementioned anatomical features, such as, for example, a mid-section of the patient including organs (e.g., colon, liver, lungs), bones (e.g., ribs, spine), muscles (e.g., abdominal muscles), and/or other anatomical features.

Furthermore, for simplicity, individual images are discussed (e.g., a diagnostic image, a model image, etc.), however, it is to be understood that aspects of the present disclosure are applicable to numerous images. For example, a CT image can illustrate an anatomical feature in two-dimensions for a specific cross-sectional location, where a plurality of CT scans can be used to collectively illustrate the anatomical feature in three dimensions.

Referring now to FIG. 1, illustrated is a block diagram of an example medical system 100 for surgical planning. The medical system 100 can include a surgical modeling system 102, a medical imaging device 104, a 3D printer 106, and a patient medical record 108 communicatively coupled to one another by a permanent, semi-permanent, or intermittent network 120. The network 120 can comprise one or more physical or wireless interconnections between surgical modeling system 102, medical imaging device 104, 3D printer 106, and patient medical record 108.

In some embodiments of the present disclosure, a diagnostic image 110 of an organ is used to create a 3D model file 112 that can be executed by 3D printer 106 to create a 3D model 114 of the organ. The 3D model 114 can include contrast materials used to indicate fiduciary points, surgical marks (e.g., incision locations, suture locations, implant locations, etc.), and/or other indicators relevant to planning a surgical procedure.

Thus, in some embodiments, surgical marks are integrated into the 3D model 114 during fabrication based on instructions contained in 3D model file 112, where the instructions are based on a physician's input about the type, location, and/or geometry of the surgical marks. In other embodiments, the surgical marks are integrated into the 3D model 114 post-fabrication by a physician (or other healthcare practitioner) manually marking the 3D model 114 using a contrast material (e.g., a marker depositing an ink with a contrast material). In yet other embodiments, some surgical marks are integrated into the 3D model 114 at fabrication and other surgical marks are made to 3D model 114 post-fabrication. In yet other embodiments, a physician can make surgical marks on the 3D model 114 by, for example, performing a mock surgery on the 3D model 114.

The medical imaging device 104 can generate a 3D model image 116 of the 3D model 114. The 3D model image 116 can show points, lines, areas, volumes, and/or other features related to fiduciary points and/or surgical marks using contrast materials. The 3D model image 116 can be superimposed with the diagnostic image 110 using the fiduciary points to orient, align, and scale the two images together to create superimposed image 118. The superimposed image 118 can be used to plan, implement, monitor, and/or review surgical procedures.

Surgical modeling system 102 can store instructions configured to select fiduciary points on diagnostic image 110, generate a 3D model file 112 which stores instructions for printing 3D model 114 at 3D printer 106, and superimpose diagnostic image 110 with 3D model image 116 to generate superimposed image 118. In some embodiments, surgical modeling system 102 comprises a computer-readable storage medium storing the superimposed image 118 and a display (e.g., monitor, user interface, screen, etc.) for presenting the superimposed image 118 to a user. Surgical modeling system 102 is discussed in more detail hereinafter with respect to FIG. 8.

Medical imaging device 104 can comprise a device configured to generate images using X-ray computed tomography (CT), computed axial tomography (CAT), X-ray radiography (e.g., fluoroscopy, projectional radiographs, etc.), magnetic resonance imaging (MRI), medical ultrasonography (e.g., ultrasound), endoscopy, elastography, photoacoustic imaging, thermography, positron emission tomography (PET), single-photon emission computed tomography (SPECT), diffuse optical tomography, electric impedance tomography, optoacoustic imaging, a different medical imaging technique, and/or a combination of the aforementioned medical imaging techniques. For simplicity, medical imaging device 104 is primarily described with respect to CT images, however, any other medical imaging technique, such as the medical imaging techniques discussed above, is within the spirit and scope of the present disclosure.

3D printer 106 can comprise a device configured to join, solidify, or otherwise formulate 3D model 114 using stereolithography (STL), photopolymerization, fused deposit modeling (FDM), fused filament fabrication, selective laser sintering, direct metal laser sintering, electron beam melting, additive manufacturing (AM), or a different technique. In some embodiments, 3D printer 106 can execute a 3D model file 112 such as, but not limited to, a STL file, a virtual reality modeling language (VRML) file (e.g., a .WRL file), an additive manufacturing file (e.g., a .AMF file), or a different file storing instructions for printing 3D model 114. 3D model file 112 can store instructions indicating at least a type of material for each point of the 3D model 114. In some embodiments 3D model file 112 can also store instructions indicating nozzle temperature, nozzle backpressure, angle of deposition, speed of translation, and other parameters relevant to fabricating 3D model 114 using 3D printer 106.

3D model 112 can be fabricated with a base material and at least one contrast material. The base material can be used to geometrically approximate (e.g., replicate, represent, etc.) an organ. The base material can comprise a polymer such as, but not limited to, acrylonitrile butadiene styrene (ABS), polylactic acid (PLA), polyvinyl alcohol (PVA), polyamides (e.g., Nylon), high density polyethylene (HDPE), polyethylene terephthalate (PETT), a thermoplastic, a thermoplastic elastomer (TPE), a different polymer, a combination of polymers, or a different material. In some embodiments, the base material comprises a material approximating the density, hardness, rigidity, and/or other physical characteristics of the anatomical feature that the 3D model 114 is replicating.

In some embodiments, the at least one contrast material can comprise a metal or alloy such as, but not limited to, titanium, tungsten, steel, a different metal, or an alloy of two or more metals. The contrast material can be applied to the 3D model 114 during fabrication and/or manually by a physician manipulating the 3D model 114 after fabrication.

In some embodiments, the at least one contrast material can comprise a polymer compounded with a loading agent. The loading agent can comprise iodine, barium sulfate, gadolinium, titanium, tungsten, zirconium oxide, a metal, an alloy, or a different material capable of providing contrast to the medical scanning device 104 (e.g., a sufficiently high radiodensity). In some embodiments, the at least one contrast material comprises a composite material comprising a polymer-matrix composite, a metal-matrix composite, or a ceramic-matrix composite. In embodiments where the composite material comprises a polymer-matrix composite, the polymer-matrix composite can include a metallic or ceramic reinforcement having a sufficiently high radiodensity to appear in medical images. The metallic or ceramic reinforcement can comprise particulate reinforcement, short fiber reinforcement, long fiber reinforcement, or continuous fiber reinforcement.

In some embodiments, a surface of 3D model 114 is marked with an ink having a sufficiently high radiodensity to appear in 3D model image 116. The ink can comprise a dye, pigment, or other additive having iodine, barium sulfate, gadolinium, titanium, tungsten, zirconium oxide, or a different contrast agent. The 3D model 114 can be marked with the ink as part of a physician preparing a surgical plan.

Patient medical record 108 can comprise an electronic health record (EHR), an electronic medical record (EMR), or a different record storing personal and medical information about an individual. In some embodiments, superimposed image 118 is saved in patient medical record 108.

FIG. 1 is intended to illustrate the major components of an example medical system 100. However, in some embodiments, medical system 100 can exhibit more or fewer components than the components shown. In some embodiments, the components illustrated in medical system 100 can have greater or lesser complexity than shown, and they can exist, if they exist at all, in alternative configurations.

Figure 2:
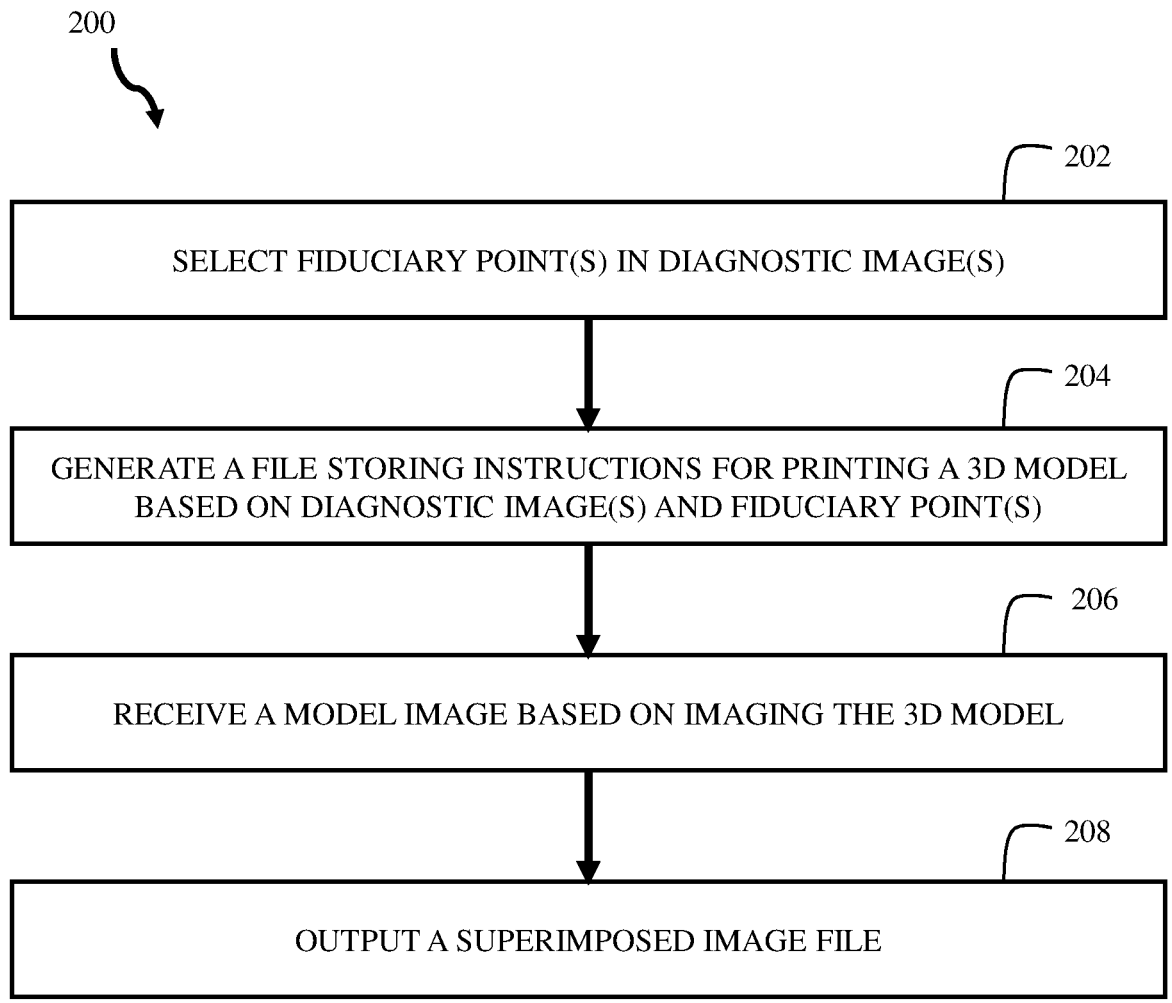
FIG. 2 illustrates a flowchart of an example method for outputting a superimposed image, in accordance with some embodiments of the present disclosure.

Referring now to FIG. 2, illustrated is a flowchart of an example method for generating a superimposed image, in accordance with some embodiments of the present disclosure. The method 200 can be performed by a surgical modeling system (e.g., surgical modeling system 102 of FIG. 1 or surgical modeling system 800 of FIG. 8) or a different configuration of hardware and/or software. For clarity, the method 200 will be described as being performed by a surgical modeling system.

In operation 202, the surgical modeling system can select fiduciary points in a diagnostic image (e.g., CT scan, MRI scan, X-ray scan, etc.) of an organ (e.g., or any anatomical structure). Fiduciary points can refer to fiducial markers, fiducials, or other indicators useful for referencing, measuring, locating, aligning, or otherwise contextualizing an image. Operation 202 is discussed in more detail hereinafter with respect to FIG. 3.

In operation 204, the surgical modeling system can generate a file storing instructions for printing a three-dimensional model (e.g., 3D model file 112 of FIG. 1) of the organ based on the diagnostic image. The file can store instructions for creating portions of the 3D model using a base material (e.g., a thermoplastic) and the fiduciary points and/or the surgical marks in the 3D model using at least one contrast material. The contrast material can be configured for visibility in a medical image (e.g., CT scan, MRI scan, X-ray scan, etc.). The file can comprise, but is not limited to, an AMF file, a WRML file, a STL file, or a different file type. The file can store instructions converting the diagnostic image to a 3D image by segmenting, compiling, repairing, and otherwise manipulating one or more diagnostic images to create a 3D image file. Operation 204 is discussed in more detail hereinafter with respect to FIG. 4.

In operation 206, the surgical modeling system can receive a model image (e.g., 3D model image 114 of FIG. 1). The model image can comprise an image of the 3D model taken by a medical imaging system (e.g., medical imaging system 104 of FIG. 1). The model image can illustrate at least one fiduciary point and at least one surgical mark. The surgical mark can be created using the first contrast material when the 3D model is fabricated and/or a second contrast material applied to the 3D model post-fabrication (e.g., an ink deposited on the surface of the 3D model). In some embodiments, the second contrast material comprises an ink that is visible in a medical image (e.g., CT scan, MRI scan, X-ray scan, etc.) and deposited on the 3D model using a pen, marker, brush, or other device. In some embodiments, the ink contains a dye, pigment, or other additive having iodine, barium sulfate, gadolinium, titanium, tungsten, zirconium oxide, or a different contrast agent.

In operation 208, the surgical modeling system can superimpose (e.g., align, orient, and/or scale) the model image from operation 206 with the diagnostic image from operation 202 using the fiduciary points to create a superimposed image (e.g., superimposed image 118 of FIG. 1). The superimposed image can show the organ from the diagnostic image together with the surgical marks from the model image.

FIG. 2 is intended to illustrate the major components of an example method for generating a superimposed image. However, in some embodiments, method 200 can exhibit more or fewer operations than the operations shown. In some embodiments, the operations illustrated in the method 200 can have greater or lesser complexity than shown, and they can exist, if they exist at all, in alternative configurations.

Figure 3:
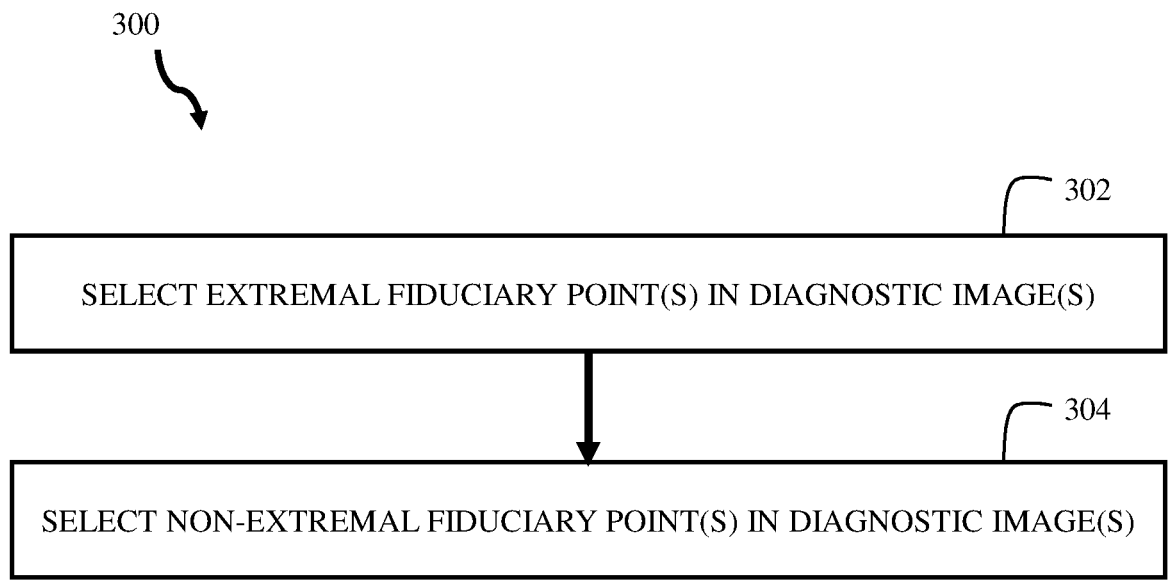
FIG. 3 illustrates a flowchart of an example method for selecting fiduciary points in a diagnostic image, in accordance with some embodiments of the present disclosure.

Referring now to FIG. 3, illustrated is a flowchart of an example method for selecting fiduciary points in a diagnostic image, in accordance with some embodiments of the present disclosure. In some embodiments, the method 300 is a sub-method of operation 202 of FIG. 2. The method 300 can be performed by a surgical modeling system (e.g., surgical modeling system 102 of FIG. 1 or surgical modeling system 800 of FIG. 8) or a different configuration of hardware and/or software. For clarity, the method 300 will be described as being performed by a surgical modeling system.

In operation 302, the surgical modeling system can select extremal fiduciary points in the diagnostic image (e.g., diagnostic image 110 of FIG. 1). Extremal fiduciary points can comprise points located on a portion of the organ illustrated in the diagnostic image having a curvature above a first threshold (e.g., 2.0 inches, 1.0 inches, 0.5 inches, etc.). The curvature of a point on a curve can be calculated as the reciprocal of a radius of an osculating circle of the point. Locations in the diagnostic image having a curvature above the first threshold are readily identifiable and verifiable. Thus, extremal fiduciary points can comprise points that can be used to create a "mesh" or another geometric model useful to creating a 3D model and/or anchoring non-extremal fiduciary points.

In operation 304, the surgical modeling system can select non-extremal fiduciary points in the diagnostic image. Non-extremal fiduciary points can comprise points located on a smooth surface having limited features for verifying and/or identifying the location of the non-extremal fiduciary points. In some embodiments, non-extremal fiduciary points are points located on an anatomical feature having a curvature below the first threshold. In some embodiments, the non-extremal fiduciary points are defined at least partly using the extremal fiduciary points.

For the purposes of the present disclosure, fiduciary points discussed in FIG. 3 can comprise points (e.g., a circle having a diameter between 0.010 inches and 0.5 inches), crosses (e.g., two equal or non-equal perpendicular lines bisecting one another), lines, or a different geometry (e.g., square, rectangle, oval, etc.).

FIG. 3 is intended to illustrate the major components of an example method for selecting fiduciary points. However, in some embodiments, the method 300 can exhibit more or fewer operations than the operations shown. In some embodiments, the operations illustrated in the method 300 can have greater or lesser complexity than shown, and they can exist, if they exist at all, in alternative configurations.

Figure 4:
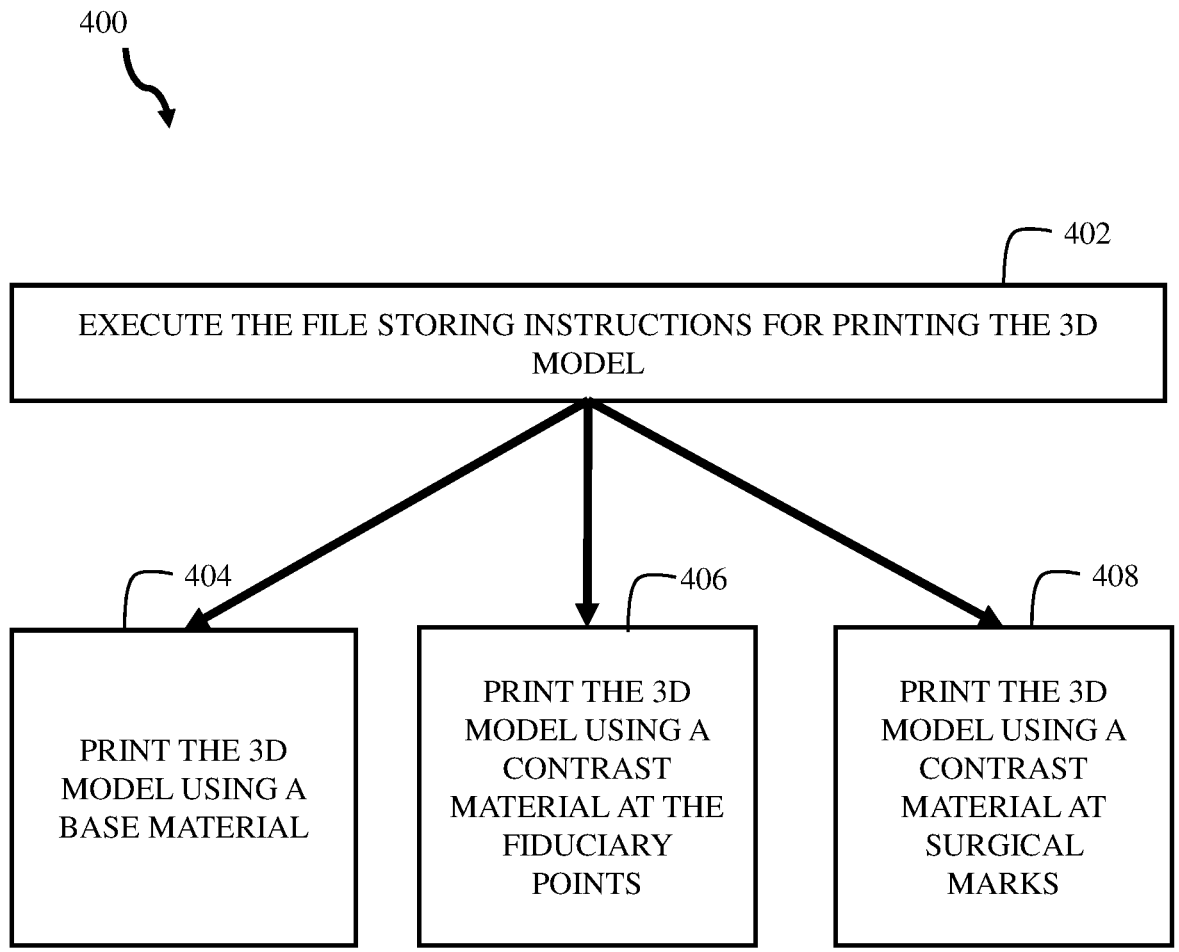
FIG. 4 illustrates a flowchart of an example method for generating a three-dimensional model, in accordance with some embodiments of the present disclosure.

Referring now to FIG. 4, illustrated is a flowchart of an example method for executing a 3D print file, in accordance with some embodiments of the present disclosure. In some embodiments, the method 400 is a sub-method of operation 204 of FIG. 2. The method 400 can be performed by a 3D printer (e.g., 3D printer 106 of FIG. 1), by a surgical modeling system (e.g., surgical modeling system 102 of FIG. 1 or surgical modeling system 800 of FIG. 8), or by a different configuration of hardware and/or software. For clarity, the method 400 will be described as being performed by a 3D printer.

In operation 402, the 3D printer can execute the file storing instructions for printing the 3D model (e.g., 3D model file 112 of FIG. 1).

In operation 404, the 3D printer can print a first portion of the model using a base material. In some embodiments, the first portion of the 3D model is a majority of the 3D model, and the base material can comprise a radiolucent material such as, but not limited to, acrylonitrile butadiene styrene (ABS), polylactic acid (PLA), polyvinyl alcohol (PVA), polyamides (e.g., Nylon), high density polyethylene (HDPE), polyethylene terephthalate (PETT), a thermoplastic, a thermoplastic elastomer (TPE), a different polymer, a combination of polymers, or a different material. In some embodiments, the base material comprises a material approximating the density, hardness, rigidity, and/or other physical characteristics of the anatomical feature that the 3D model is replicating.

In operation 406, the 3D printer can print a second portion of the model using a contrast material. The second portion can comprise the fiduciary points. In some embodiments, the contrast material can comprise a material having a high radiodensity such that the contrast material is visible on an image generated by a medical imaging system (e.g., medical imaging system 104 of FIG. 1) of the 3D model. For example, the contrast material can be a metal or alloy such as, but not limited to, titanium, tungsten, steel, a different metal, or an alloy of two or more metals that would appear in, for example, a CT image. In some embodiments, the at least one contrast material can comprise a polymer compounded with a loading agent. The loading agent can comprise iodine, barium sulfate, gadolinium, titanium, tungsten, zirconium oxide, or a different material capable of providing contrast to the medical scanning device 104 (e.g., a sufficiently high radiodensity). In some embodiments, the at least one contrast material comprises a composite material comprising a polymer-matrix composite, a metal-matrix composite, or a ceramic-matrix composite. In embodiments where the composite material comprises a polymer-matrix composite, the polymer-matrix composite can include a metallic or ceramic reinforcement having a sufficiently high radiodensity to appear in medical images. The metallic or ceramic reinforcement can comprise particulate reinforcement, short fiber reinforcement, long fiber reinforcement, or continuous fiber reinforcement.

In operation 408, the 3D printer can print a third portion of the 3D model using a contrast material. The third portion of the 3D model can comprise surgical marks (e.g., points, lines, areas, volumes, etc.). The surgical marks can be integrated into the 3D model to represent incisions, implants, extractions, points representing locations, lines representing lengths, angles, widths, and/or depths, surfaces representing angles, lengths, widths, and/or depths, identification points, or other points useful for planning and performing a surgical operation. In various embodiments, the contrast material used in operation 406 and the contrast material used in operation 408 can be similar or different contrast materials.

As shown in FIG. 4, operations 404, 406, and 408 can occur contemporaneously. In some embodiments, the 3D printer uses two separate printing nozzles where a first printing nozzle prints the base material in operation 404 and a second printing nozzle prints the contrast material in operations 406 and 408.

FIG. 4 is intended to illustrate the major components of an example method for executing a 3D print file, in accordance with some embodiments of the present disclosure. However, in some embodiments, the method 400 can exhibit more or fewer operations than the operations shown. In some embodiments, the operations illustrated in the method 400 can have greater or lesser complexity than shown, and they can exist, if they exist at all, in alternative configurations.

Figure 5:
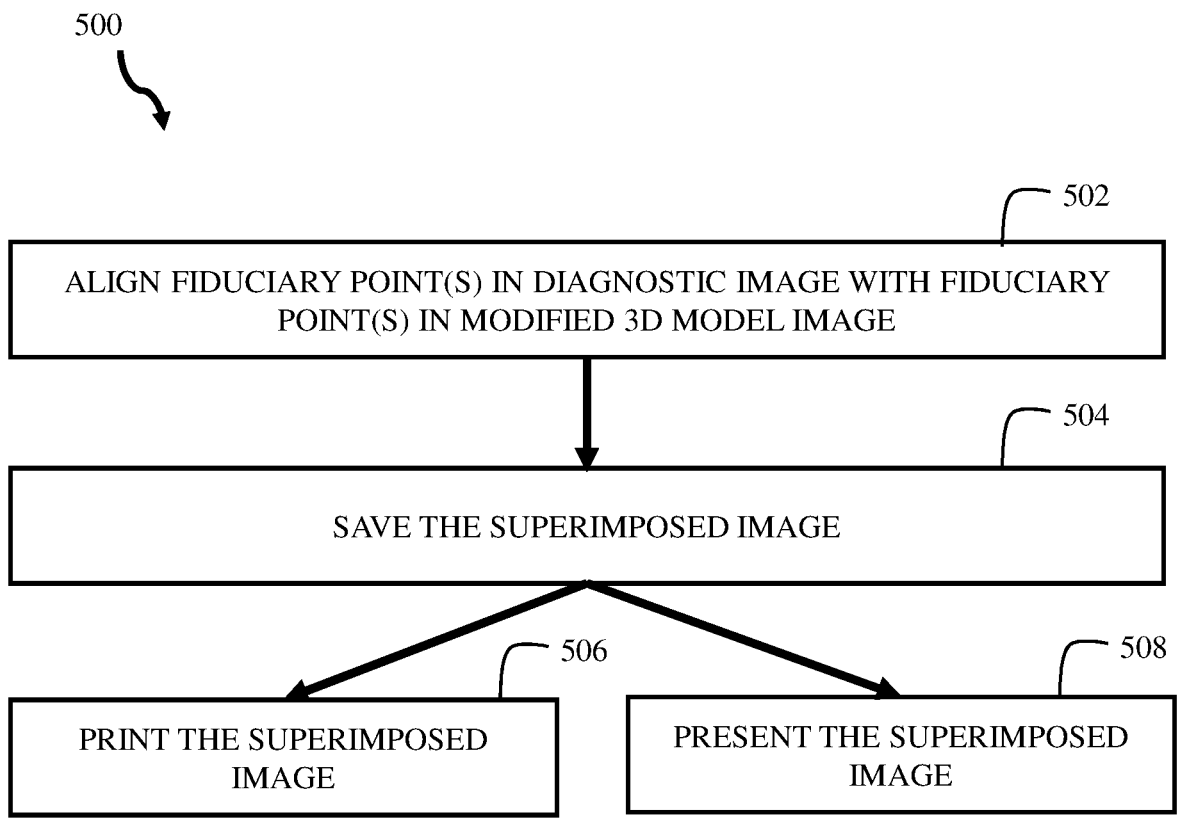
FIG. 5 illustrates a flowchart of an example method for aligning a diagnostic image and a model image, in accordance with some embodiments of the present disclosure.

Referring now to FIG. 5, illustrated is a flowchart of an example method for saving a superimposed image, in accordance with some embodiments of the present disclosure. In some embodiments, the method 500 is a sub-method of operation 208 of FIG. 2. The method 500 can be performed by a surgical modeling system (e.g., surgical modeling system 102 of FIG. 1 or surgical modeling system 800 of FIG. 8) or a different configuration of hardware and/or software. For clarity, the method 500 will be described as being performed by a surgical modeling system.

In operation 502, the surgical modeling system can align a first set of fiduciary points in a diagnostic image with a second set of fiduciary points in a model image. The diagnostic image can be the diagnostic image from operation 202 of FIG. 2 and/or diagnostic image 110 of FIG. 1. The model image can be the model image from operation 206 of FIG. 2 and/or 3D model image 114 of FIG. 1. Operation 502 can comprise aligning (e.g., translation operations), orienting (e.g., rotation operations), and/or sizing (e.g., scaling operations) until the first set of fiduciary points sufficiently matches (e.g., overlaps) with the second set of fiduciary points.

In operation 504, the surgical modeling system can save the superimposed image. In some embodiments, the superimposed image is saved in a patient medical record (e.g., patient medical record 108 of FIG. 1). In some embodiments, the superimposed image is saved in a different medical database. In some embodiments, the superimposed image is saved in a computer readable storage medium.

In operation 506, the surgical modeling system can print the superimposed image. In some embodiments, the printed superimposed image comprises a radiograph or different graphic that can be backlit by a lightbox to accentuate the details of the printed superimposed image.

In operation 508, the surgical modeling system can present the superimposed image on a display (e.g., a monitor, a user interface, a screen, etc.). In some embodiments, a healthcare practitioner reviews the superimposed image to plan a surgical procedure and/or review the accuracy of a completed surgical procedure.

Operations 506 and 508 need not both occur, and embodiments exist where only one of operation 506 or operation 508 occurs, where both operations 506 and 508 occur, and/or where neither operation 506 nor operation 508 occurs.

FIG. 5 is intended to illustrate the major components of an example method for creating a superimposed image, in accordance with some embodiments of the present disclosure. However, in some embodiments, the method 500 can exhibit more or fewer operations than the operations shown. In some embodiments, the operations illustrated in the method 500 can have greater or lesser complexity than shown, and they can exist, if they exist at all, in alternative configurations.

Figure 6A:
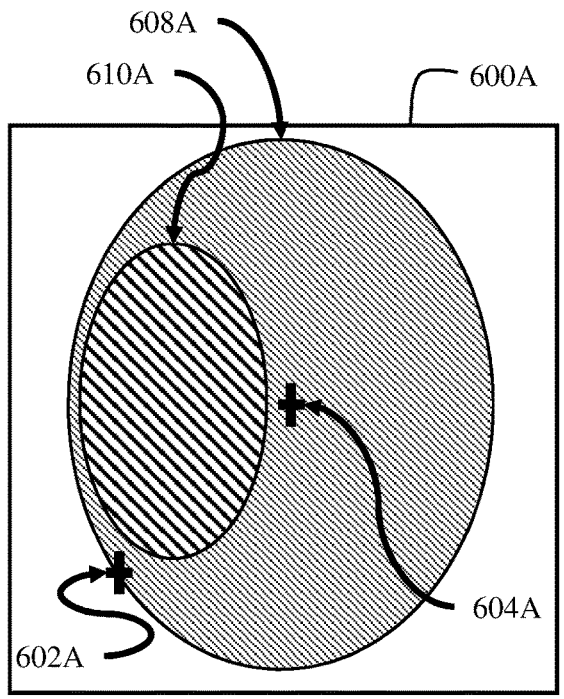
FIG. 6A illustrates an example diagnostic image, in accordance with some embodiments of the present disclosure.

FIG. 6A illustrates an example diagnostic image, in accordance with some embodiments of the present disclosure. In some embodiments, diagnostic image 600A is consistent with diagnostic image 110 of FIG. 1. In some embodiments, diagnostic image 600A illustrates one or more anatomical structures 608A, 610A such as organs, bones, muscles, tendons, ligaments, and/or other anatomical features. Diagnostic image 600A is a simplified image shown for illustrative purposes, and diagnostic image 600A can comprise more features than the features shown in more geometries than the geometries shown and with greater resolution than the resolution shown. Diagnostic image 600A includes an extremal fiduciary point 602A and a non-extremal fiduciary point 604A. In some embodiments, extremal fiduciary point 602A and non-extremal fiduciary point 604A are selected in operation 202 of FIG. 2 and/or operations 302 and 304 of FIG. 3. Although extremal fiduciary point 602A and non-extremal fiduciary point 604A are shown as crosses, the fiduciary points can be any geometry (e.g., circle, square, rectangle, etc.). As can be seen in diagnostic image 600A, extremal fiduciary point 602A is located on a first portion of anatomical structure 608A having a curvature above a threshold. In contrast, non-extremal fiduciary point 604A is shown on a second portion of anatomical structure 608A with a curvature below the threshold. In some embodiments, non-extremal fiduciary point 604A can have a location defined partly by extremal fiduciary point 602A. Although only one extremal fiduciary point 602A and one non-extremal fiduciary point 604A are shown, in some embodiments, many of each type of fiduciary points exist (e.g., several, tens, or hundreds).

Figure 6B:
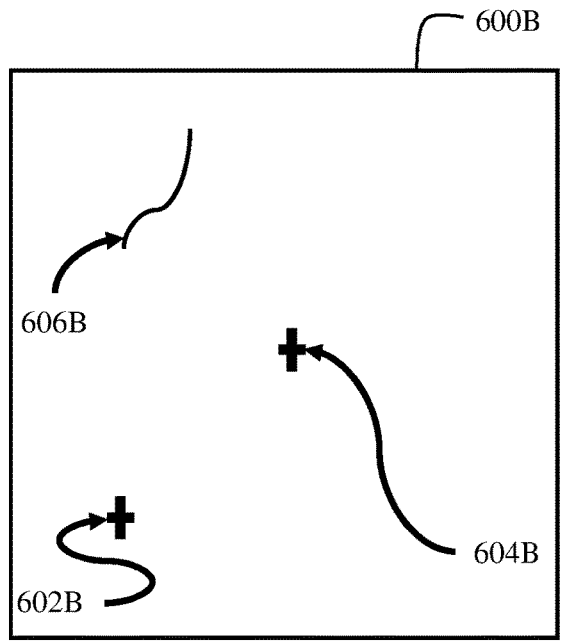
FIG. 6B illustrates an example model image, in accordance with some embodiments of the present disclosure.

FIG. 6B illustrates an example model image, in accordance with some embodiments of the present disclosure. Model image 600B can be consistent with 3D model image 114 of FIG. 1. In some embodiments, the model image 600B is an image based on a 3D model (e.g., 3D model 114 of FIG. 1) created by executing instructions in a file generated in operation 204 of FIG. 2 and/or the method 400 of FIG. 4. In some embodiments, the 3D model comprises a base material that can be radiolucent or otherwise invisible or minimally visible to a medical imaging system (and thus, not shown in model image 600B). In some embodiments, model image 600B comprises at least one extremal fiduciary point 602B and at least one non-extremal fiduciary point 604B. Extremal fiduciary point 602B and non-extremal fiduciary point 604B can correspond to portions of the 3D model printed using a contrast material (e.g., a metallic material).

In some embodiments, model image 600B further comprises at least one surgical mark 606B. Surgical mark 606B can indicate locations, features, or other useful information for planning a surgery. Surgical mark 606B can correspond to portions of the three-dimensional model printed using a contrast material and/or portions on the surface of the three-dimensional model marked by a scan-opaque ink (e.g., an ink having a pigment, dye, or other additive having radiodensity properties sufficiently high to be visible during medical imaging). Surgical mark 606B can be based on physician input as part of a physician's pre-surgical plan.

Figure 6C:
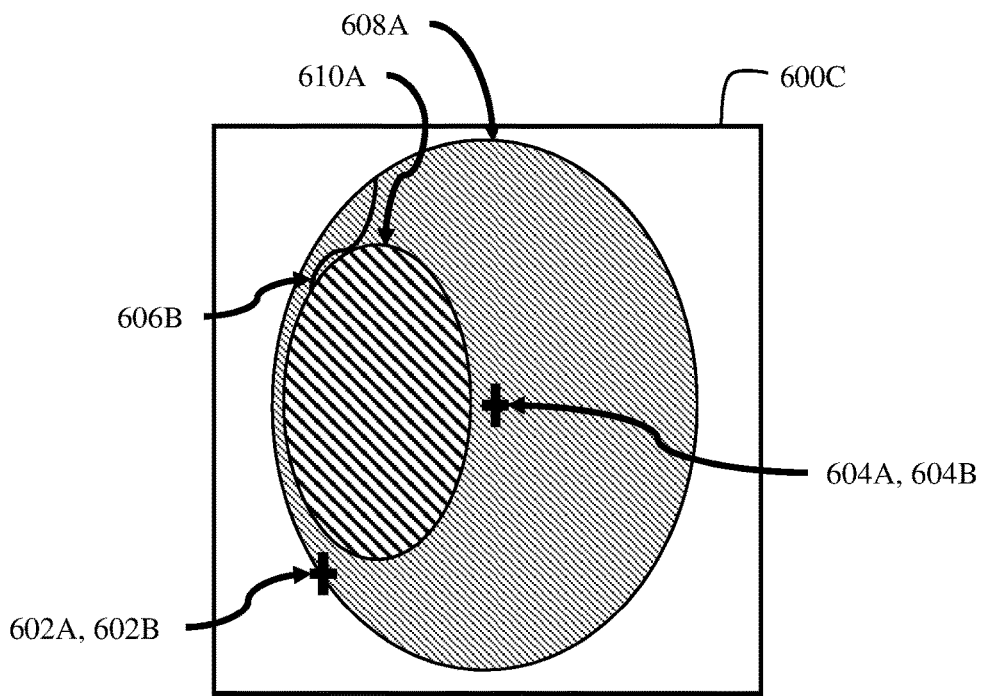
FIG. 6C illustrates an example superimposed image, in accordance with some embodiments of the present disclosure.

FIG. 6C illustrates an example superimposed image 600C, in accordance with some embodiments of the present disclosure. Superimposed image 600C can be consistent with superimposed image 118 of FIG. 1. Superimposed image 600C can comprise the diagnostic image 600A aligned, oriented, and scaled to the model image 600B at extremal fiduciary points 602A, 602B and non-extremal fiduciary points 604A, 604B. Superimposed image 600C can further illustrate surgical mark 606B from model image 600B and anatomical structures 608A, 610A from diagnostic image 600A.

In some embodiments, superimposed image 600C is presented on a display (e.g., a monitor, a user interface, a screen, etc.) so that a healthcare practitioner can better plan, evaluate, and/or review a medical procedure.

FIGS. 6A-6C are intended to illustrate the major components of an example diagnostic image 600A, model image 600B, and superimposed image 600C in accordance with some embodiments of the present disclosure. However, in some embodiments, the FIGS. 6A-6C can exhibit more or fewer components than the components shown. In some embodiments, the components illustrated in FIGS. 6A-6C can have greater or lesser complexity than shown, and they can exist, if they exist at all, in alternative configurations.

Figure 7:
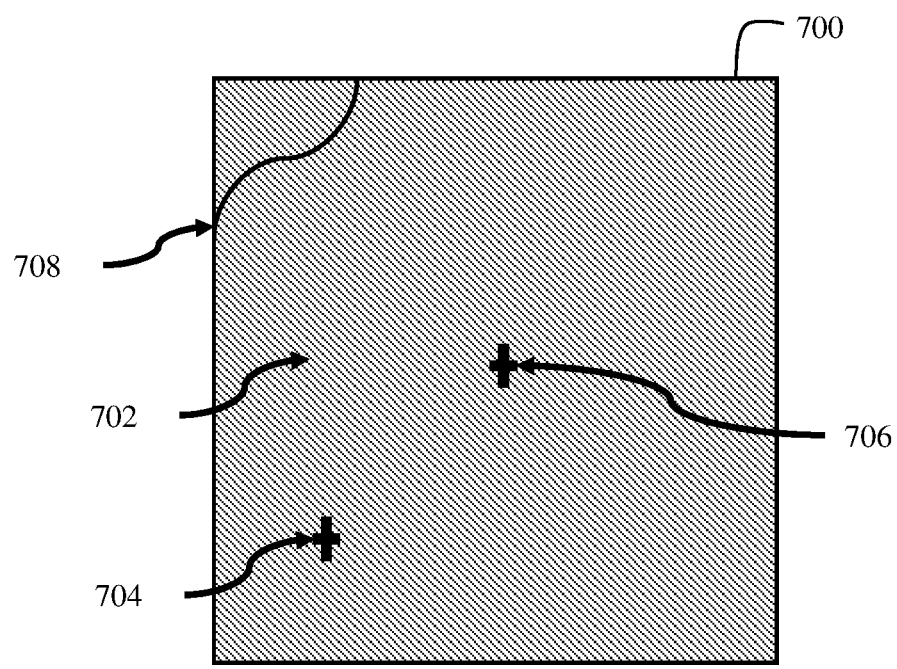
FIG. 7 illustrates an example cross-section of a three-dimensional model, in accordance with some embodiments of the present disclosure.

FIG. 7 illustrates an example cross-sectional view of a portion of a three-dimensional model, in accordance with some embodiments of the present disclosure. Cross-sectional view 700 is a simplified view of a portion of a 3D model such that the entire perimeter of the 3D model is not shown. Cross-sectional view 700 includes base material 702, fiduciary points 704, 706, and surgical mark 708. Base material 702 can comprise, but is not limited to, acrylonitrile butadiene styrene (ABS), polylactic acid (PLA), polyvinyl alcohol (PVA), polyamides (e.g., Nylon), high density polyethylene (HDPE), polyethylene terephthalate (PETT), a thermoplastic, a thermoplastic elastomer (TPE), or a different material. In some embodiments, the base material 702 comprises a material having properties (e.g., density, modulus, hardness, etc.) similar to the organ being replicated. In some embodiments, base material 702 can substantially approximate a geometry of an organ.

Fiduciary points 704, 706 and surgical mark 708 can comprise a contrast material such as, but not limited to, a metal (e.g., titanium, tungsten, steel), an alloy of two or more metals, or a composite material. In embodiments where fiduciary points 704, 706, and surgical mark 708 are a composite material, the composite material can comprise a polymer-matrix composite, a metal-matrix composite, or a ceramic-matrix composite. In embodiments where the composite material comprises a polymer-matrix composite, the polymer-matrix composite can include a metallic or ceramic reinforcement having a sufficiently high radiodensity to appear in medical images. The metallic or ceramic reinforcement can comprise particulate reinforcement, short fiber reinforcement, long fiber reinforcement, or continuous fiber reinforcement.

Although fiduciary points 704, 706 are shown as crosses, fiduciary points can be any other geometry (e.g., points, circles, ovals, squares, rectangles, etc.). Although fiduciary points 704, 706 are shown in two dimensions for illustrative purposes, in some embodiments, fiduciary points 704, 706 comprise three dimensional objects having a volume (e.g., a spherical fiduciary point, a cubical fiduciary point, etc.). Although surgical mark 708 is shown as a line, surgical mark 708 can alternatively be a point, an area, a volume, or a different feature. Furthermore, although a solid line is shown in surgical mark 708, surgical mark 708 can likewise include patterns useful for indicating different aspects of a surgical operation (e.g., a dashed line). Surgical mark 708 can be integrated as part of the manufacture of the 3D model or subsequent to manufacture of the 3D model by a physician manipulating the model (e.g., performing a mock surgical procedure on the 3D model).

Although not shown, cross-sectional view 700 can also include a portion of a mark on a surface of the 3D model made by an ink having an additive with sufficient properties to be visible in a medical image (e.g., a CT scan) of the 3D model. The ink can be applied by a physician as part of the pre-surgical planning process.

FIG. 7 is intended to illustrate the major components of an example cross-sectional view 700 of a 3D model in accordance with some embodiments of the present disclosure. However, in some embodiments, cross-sectional view 700 can exhibit more or fewer features than the features shown. In some embodiments, the features illustrated in FIG. 7 can have greater or lesser complexity than shown, and they can exist, if they exist at all, in alternative configurations.

Figure 8:
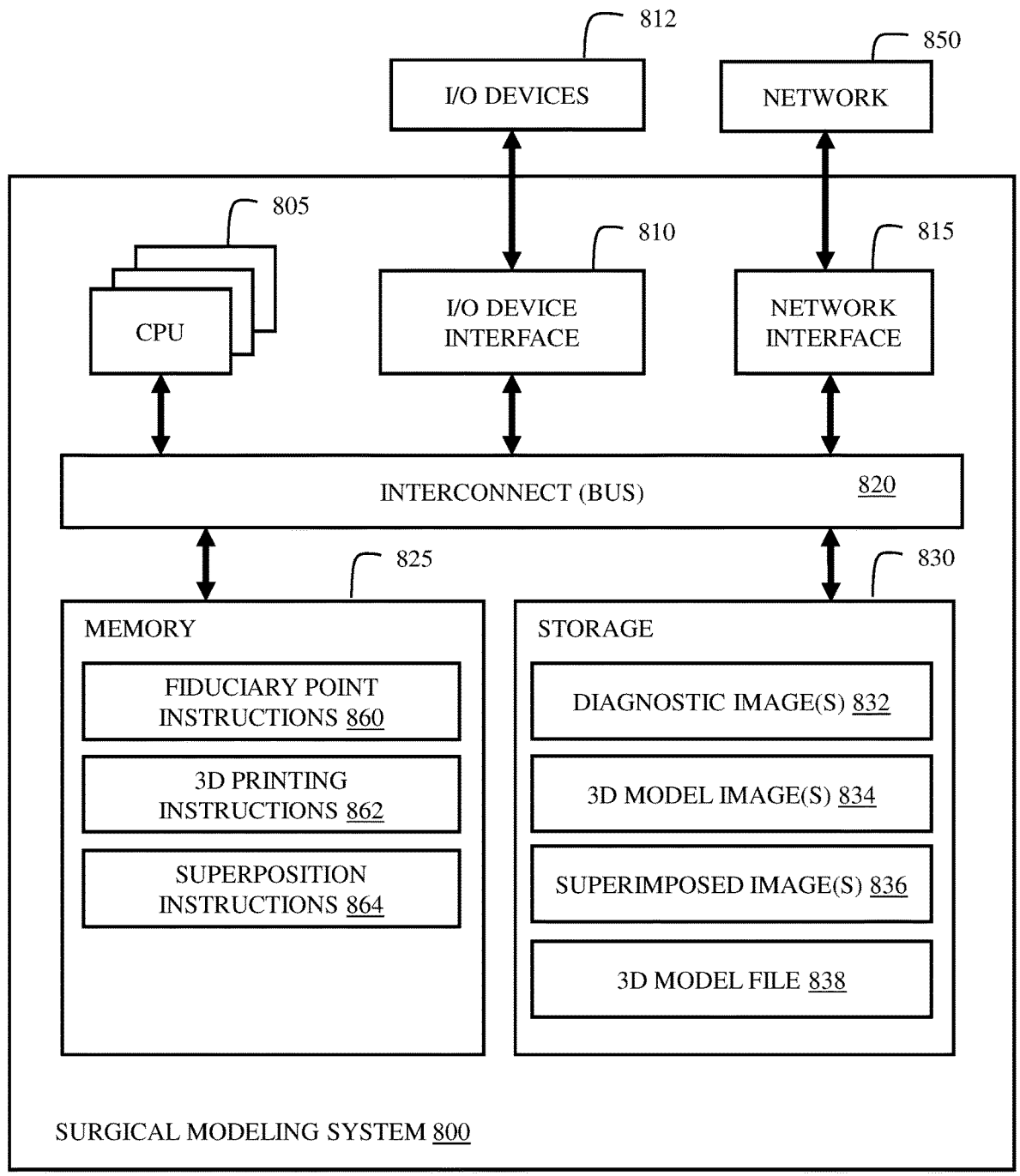
FIG. 8 illustrates a block diagram of an example surgical modeling system, in accordance with some embodiments of the present disclosure.

FIG. 8 illustrates a block diagram of an example surgical modeling system 800 in accordance with some embodiments of the present disclosure. In various embodiments, surgical modeling system 800 performs any of the methods described in FIGS. 2-5. In some embodiments, surgical modeling system 800 provides instructions for one or more of the methods described in FIGS. 2-5 to a client machine such that the client machine executes the method, or a portion of the method, based on the instructions provided by the surgical modeling system 800 (e.g., surgical modeling system 800 can provide 3D printing instructions 862 for a three-dimensional model to a 3D printer to be printed at the 3D printer).

The surgical modeling system 800 includes a memory 825, storage 830, an interconnect (e.g., BUS) 820, one or more CPUs 805 (also referred to as processors 805 herein), an I/O device interface 810, I/O devices 812, and a network interface 815.

Each CPU 805 retrieves and executes programming instructions stored in the memory 825 or storage 830. The interconnect 820 is used to move data, such as programming instructions, between the CPUs 805, I/O device interface 810, storage 830, network interface 815, and memory 825. The interconnect 820 can be implemented using one or more busses. The CPUs 805 can be a single CPU, multiple CPUs, or a single CPU having multiple processing cores in various embodiments. In some embodiments, a CPU 805 can be a digital signal processor (DSP). In some embodiments, CPU 805 includes one or more 3D integrated circuits (3DICs) (e.g., 3D wafer-level packaging (3DWLP), 3D interposer based integration, 3D stacked ICs (3D-SICs), monolithic 3D ICs, 3D heterogeneous integration, 3D system in package (3DSiP), and/or package on package (PoP) CPU configurations). Memory 825 is generally included to be representative of a random access memory (e.g., static random access memory (SRAM), dynamic random access memory (DRAM), or Flash). The storage 830 is generally included to be representative of a non-volatile memory, such as a hard disk drive, solid state device (SSD), removable memory cards, optical storage, or flash memory devices. In an alternative embodiment, the storage 830 can be replaced by storage area-network (SAN) devices, the cloud, or other devices connected to the surgical modeling system 800 via the I/O device interface 810 or a network 850 via the network interface 815.

In some embodiments, the memory 825 stores fiduciary point instructions 860, 3D printing instructions 862, and superposition instructions 864 and the storage 830 stores diagnostic image 832, 3D model image 834, superimposed image 836, and 3D model file 838. However, in various embodiments, the fiduciary point instructions 860, 3D printing instructions 862, superposition instructions 864, diagnostic image 832, 3D model image 834, superimposed image 836, and 3D model file 838 are stored partially in memory 825 and partially in storage 830, or they are stored entirely in memory 825 or entirely in storage 830, or they are accessed over a network 850 via the network interface 815.

Fiduciary point instructions 860 can comprise processor-executable instructions configured to perform operation 202 of FIG. 2 and/or the method 300 of FIG. 3. 3D printing instructions 862 can comprise processor-executable instructions configured to perform the method 400 of FIG. 4. Superposition instructions 864 can comprise processor-executable instructions for performing the method 200 of FIG. 2 and/or the method 500 of FIG. 5.

Diagnostic image 832 can be consistent with diagnostic image 110 of FIG. 1. Diagnostic image 832 can comprise one or more images of an anatomical feature of a patient generated by a medical imaging device such as, but not limited to, a device configured for X-ray computed tomography (CT), computed axial tomography (CAT), X-ray radiography (e.g., fluoroscopy, projectional radiographs, etc.), magnetic resonance imaging (MRI), medical ultrasonography (e.g., ultrasound), endoscopy, elastography, photoacoustic imaging, thermography, positron emission tomography (PET), single-photon emission computed tomography (SPECT), diffuse optical tomography, electric impedance tomography, optoacoustic imaging, a different medical imaging technique, and/or a combination of the aforementioned medical imaging techniques.

3D model image 834 can be consistent with 3D model image 114 of FIG. 1. 3D model image 834 can comprise one or more images generated by a medical imaging device of a 3D model of the anatomical feature of the patient. The 3D model image 834 can comprise, but is not limited to, a CT scan, a MRI scan, a X-ray scan, or a different medical image.

Superimposed image 836 can be consistent with superimposed image 118 of FIG. 1. Superimposed image 836 can comprise one or more images, where each image combines a diagnostic image 832 corresponding to a 3D model image 834. Superimposed image 836 can be useful for planning surgical operations, acting as a guide during surgical operations, and/or comparing a pre-surgical plan to a post-operative outcome.

3D model file 838 can be consistent with 3D model file 112 of FIG. 1. 3D model file 838 can comprise a computer-executable file storing instructions for printing a 3D model of an organ based on information from one or more diagnostic images.

In various embodiments, the I/O devices 812 include an interface capable of presenting information and receiving input. For example, I/O devices 812 can present information to a user interacting with surgical modeling system 800 and receive input from the user. In some embodiments, I/O devices 812 further comprise a screen for viewing any of the diagnostic image 832, the 3D model image 834, and/or the superimposed image 836. In some embodiments, I/O devices 812 further comprise a printer for printing a radiograph or other medical graphic of the superimposed image 836. In some embodiments, I/O devices 812 further comprises a 3D printer for executing 3D model file 838 to fabricate/manufacture a 3D model.

Surgical modeling system 800 is connected to the network 850 via the network interface 815. Network 850 can comprise a physical, wireless, cellular, or different network.

FIG. 8 is intended to represent the major components of an example surgical modeling system 800 according to embodiments of the present disclosure. In some embodiments, however, individual components can have greater or lesser complexity than shown in FIG. 8, and components other than, or in addition to, those shown in FIG. 8 can be present. Furthermore, in some embodiments, various components illustrated in FIG. 8 can have greater, lesser, or different functionality than shown in FIG. 8.

Embodiments of the present invention can be a system, a method, and/or a computer program product at any possible technical detail level of integration. The computer program product can include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions can be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions can also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or subset of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While it is understood that the process software (e.g., any of the instructions stored in instructions 860, 862, 864 of FIG. 8 and/or any software configured to perform any subset of the methods described with respect to FIGS. 2-5) can be deployed by manually loading it directly in the client, server, and proxy computers via loading a storage medium such as a CD, DVD, etc., the process software can also be automatically or semi-automatically deployed into a computer system by sending the process software to a central server or a group of central servers. The process software is then downloaded into the client computers that will execute the process software. Alternatively, the process software is sent directly to the client system via e-mail. The process software is then either detached to a directory or loaded into a directory by executing a set of program instructions that detaches the process software into a directory. Another alternative is to send the process software directly to a directory on the client computer hard drive. When there are proxy servers, the process will select the proxy server code, determine on which computers to place the proxy servers' code, transmit the proxy server code, and then install the proxy server code on the proxy computer. The process software will be transmitted to the proxy server, and then it will be stored on the proxy server.

Embodiments of the present invention can also be delivered as part of a service engagement with a client corporation, nonprofit organization, government entity, internal organizational structure, or the like. These embodiments can include configuring a computer system to perform, and deploying software, hardware, and web services that implement, some or all of the methods described herein. These embodiments can also include analyzing the client's operations, creating recommendations responsive to the analysis, building systems that implement subsets of the recommendations, integrating the systems into existing processes and infrastructure, metering use of the systems, allocating expenses to users of the systems, and billing, invoicing (e.g., generating an invoice), or otherwise receiving payment for use of the systems.

What is claimed is:

1. A computer-implemented method comprising:
   selecting a plurality of fiduciary points on a diagnostic image of an organ;
   generating a file storing instructions for printing, by additive manufacturing, a three-dimensional model of the organ based on the diagnostic image, wherein the file stores instructions for a base material and a first contrast material, wherein the file stores instructions for printing the plurality of fiduciary points and a surgical mark using the first contrast material;
   receiving a model image of the three-dimensional model, wherein the first contrast material is visible in the model image; and
   outputting a superimposed image file by superimposing the diagnostic image with the model image using the plurality of fiduciary points.

2. The method of claim 1, wherein the plurality of fiduciary points comprises an extremal fiduciary point in the diagnostic image of the organ located on a first portion of the organ having a curvature above a first threshold.

3. The method of claim 2, wherein the plurality of fiduciary points comprises a non-extremal fiduciary point in the diagnostic image of the organ located on a second portion of the organ having a second curvature below the first threshold, wherein the non-extremal fiduciary point has a location defined, in part, by the extremal fiduciary point.

4. The method of claim 1, wherein the first contrast material comprises a metallic material.

5. The method of claim 1, wherein the first contrast material comprises a composite material, wherein the composite material comprises a polymer matrix and a reinforcement, wherein the reinforcement is selected from the group consisting of: a metal, and a ceramic.

6. The method of claim 1, wherein a second contrast material is visible in the model image, wherein the second contrast material comprises an ink having an additive, wherein a surface of the three-dimensional model is marked using the ink, and wherein the additive is selected from the group consisting of: iodine, barium sulfate, gadolinium, and metal.

7. The method of claim 1, wherein outputting the superimposed image file further comprises:
respectively matching fiduciary points in the diagnostic image with fiduciary points in the model image; and
saving the superimposed image file in a patient medical record.

8. The method of claim 1, wherein the diagnostic image and the model image each comprise a respective computed tomography (CT) image.

9. A system comprising:
a user interface;
a processor; and
a computer-readable storage medium storing program instructions, which, when executed by the processor a configured to cause the processor to perform a method comprising:
aligning a first plurality of fiduciary points of a diagnostic image with a second plurality of fiduciary points of a model image to create a superimposed image, wherein the diagnostic image illustrates an anatomical structure, wherein the model image illustrates a surgical mark;
saving the superimposed image in the computer-readable storage medium; and
displaying the superimposed image on the user interface;
wherein the model image comprises an image of a three-dimensional model fabricated by additive manufacturing and replicating the anatomical structure, wherein the second plurality of fiduciary points and the surgical mark comprise a contrast material integrated in the three-dimensional model.

10. The system of claim 9, wherein the first plurality of fiduciary points comprises an extremal fiduciary point in the diagnostic image and located on a first portion of the anatomical structure having a curvature above a first threshold.

11. The system of claim 10, wherein the first plurality of fiduciary points comprises a non-extremal fiduciary point in the diagnostic image and located on a second portion of the anatomical structure having a second curvature below the first threshold, wherein the non-extremal fiduciary point has a location defined, in part, by the extremal fiduciary point.

12. The system of claim 9, wherein the contrast material comprises a metallic material.

13. The system of claim 9, wherein the contrast material comprises a composite material, wherein the composite material comprises a polymer matrix and a reinforcement, wherein the reinforcement is selected from the group consisting of: a metal, and a ceramic.

14. The system of claim 9, wherein the model image further comprises a second surgical mark based on a second contrast material integrated on a surface of the three-dimensional model, wherein the second contrast material comprises an ink having an additive, wherein the additive is selected from the group consisting of: iodine, barium sulfate, gadolinium, and metal.

15. The system of claim 9, wherein the three-dimensional model further comprises a radiolucent base material.

16. The system of claim 9, wherein the diagnostic image and the model image each comprise a respective computed tomography (CT) image.

17. An apparatus comprising:
a three-dimensional model fabricated by additive manufacturing, wherein the three-dimensional model comprises:
a thermoplastic base material geometrically approximating an organ;
a plurality of fiduciary points integrated in the three-dimensional model, wherein the plurality of fiduciary points comprises a first contrast material; and
a first surgical mark integrated in the three-dimensional model, wherein the first surgical mark comprises a second contrast material.

18. The apparatus of claim 17, wherein the first surgical mark is on a surface of the three-dimensional model, wherein the second contrast material comprises an ink having an additive, wherein the additive is selected from the group consisting of: iodine, barium sulfate, gadolinium, and metal.

19. The apparatus of claim 18, wherein the first contrast material and the second contrast material are visible in a computed tomography (CT) scan.

20. The apparatus of claim 17, wherein the first contrast material comprises a metallic material.

* * * * *